(12) United States Patent
Westphal et al.

(10) Patent No.: US 11,129,525 B2
(45) Date of Patent: Sep. 28, 2021

(54) METHOD FOR SELF-EXAMINATION OF AN EYE AND OPHTHALMOLOGICAL SELF-EXAMINATION APPARATUS

(71) Applicant: Carl Zeiss Meditec AG, Jena (DE)

(72) Inventors: Peter Westphal, Jena (DE); Tobias Schmitt-Manderbach, Jena (DE); Daniel Bublitz, Rausdorf (DE); Peter Klopfleisch, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 141 days.

(21) Appl. No.: 16/348,094

(22) PCT Filed: Nov. 7, 2017

(86) PCT No.: PCT/EP2017/078403
§ 371 (c)(1),
(2) Date: May 7, 2019

(87) PCT Pub. No.: WO2018/083323
PCT Pub. Date: May 11, 2018

(65) Prior Publication Data
US 2019/0254514 A1    Aug. 22, 2019

(30) Foreign Application Priority Data
Nov. 7, 2016   (DE) ..................... 10 2016 121 246.6

(51) Int. Cl.
*A61B 3/02* (2006.01)
*A61B 3/12* (2006.01)
(Continued)

(52) U.S. Cl.
CPC .............. *A61B 3/02* (2013.01); *A61B 3/0016* (2013.01); *A61B 3/0075* (2013.01);
(Continued)

(58) Field of Classification Search
CPC .... A61B 3/00; A61B 3/10; A61B 3/12; A61B 3/02; A61B 3/102; A61B 3/1025;
(Continued)

(56) References Cited

U.S. PATENT DOCUMENTS

| 2006/0114411 A1 | 6/2006 | Wei et al. |
| 2008/0100612 A1 | 5/2008 | Dastmalchi et al. |

(Continued)

FOREIGN PATENT DOCUMENTS

| CN | 101072534 A | 11/2007 |
| CN | 102970919 A | 3/2013 |

(Continued)

OTHER PUBLICATIONS

International Search Report and Written Opinion of the ISA for International Application No. PCT/EP2017/078403, dated Feb. 23, 2018; 3 pages.

(Continued)

*Primary Examiner* — Jie Lei
(74) *Attorney, Agent, or Firm* — Patterson Thuente Pedersen, P.A.

(57) ABSTRACT

The invention relates to a method for examining an eye of a patient by the patient themselves by means of an ophthalmological apparatus, said apparatus having front optics and an apparatus pupil. According to said method, the patient positions the ophthalmological apparatus relative to the eye, a measure of the deviation of the pupil of the eye from the apparatus pupil is determined, and a pupil correction signal is produced depending on the measure of the deviation, said pupil correction signal specifying a direction and/or a degree of the deviation and being output to the patient. The patient can use the pupil correction signal for repositioning in relation to the ophthalmological apparatus with a smaller deviation.

17 Claims, 6 Drawing Sheets

(51) Int. Cl.
*A61B 3/10* (2006.01)
*A61B 3/00* (2006.01)

(52) U.S. Cl.
CPC .......... *A61B 3/0083* (2013.01); *A61B 3/0091* (2013.01); *A61B 3/102* (2013.01); *A61B 3/1225* (2013.01)

(58) Field of Classification Search
CPC ... A61B 3/1225; A61B 3/0016; A61B 3/0025; A61B 3/0041; A61B 3/0075; A61B 3/0091; A61B 3/0083; A61B 3/15; A61B 3/152; A61B 3/113; A61B 3/117
USPC ........ 351/223, 221, 206, 208, 210, 211, 246
See application file for complete search history.

(56) References Cited

U.S. PATENT DOCUMENTS

| | | |
|---|---|---|
| 2011/0299034 A1 | 12/2011 | Walsh et al. |
| 2013/0093997 A1 | 4/2013 | Utsunomiya et al. |
| 2013/0194581 A1 | 8/2013 | Yoshida |
| 2013/0265545 A1 | 10/2013 | Buckland et al. |
| 2014/0132927 A1 | 5/2014 | Yamashita |
| 2015/0085253 A1 | 3/2015 | Yamazaki et al. |
| 2015/0282707 A1 | 10/2015 | Tanabe et al. |
| 2015/0313467 A1 | 11/2015 | Sakai et al. |
| 2016/0120405 A1 | 5/2016 | Tokuda et al. |
| 2016/0128569 A1 | 5/2016 | Cheng et al. |
| 2016/0148049 A1 | 5/2016 | Yu et al. |

FOREIGN PATENT DOCUMENTS

| | | |
|---|---|---|
| CN | 103222852 A | 7/2013 |
| CN | 103501406 A | 1/2014 |
| CN | 103799966 A | 5/2014 |
| CN | 104334072 A | 2/2015 |
| CN | 105581771 A | 5/2016 |
| EP | 2926722 A1 | 10/2015 |
| JP | 2016-049367 A | 4/2016 |
| JP | 2016086838 A | 5/2016 |
| WO | WO 2010/009447 A2 | 1/2010 |

OTHER PUBLICATIONS

English translation of International Search Report for International Application No. PCT/EP2017/078403, dated Feb. 23, 2018; 2 pages.

Eurotimes, Dec. 2015/Jan. 2016, "Ocular Imaging—Binocular OCT device seeks to reinvent eye examinations", pp. 14-15.

"Optical Coherence Tomography—Technology and Applications", Editors: Prof. Dr. Wolfgang Drexler, Prof. Dr. James G. Fujimoto, Springer International Publishing AG, ISBN: 978-3-540-77550-8 (Online).

Drexler et al., "Optical Coherence Tomography—Technology and Applications", Biological and Medical Physics, Biomedical Engineering, Spring International Publishing AG, ISBN: 978-3-540-77550-8, (Online), Mar. 2008, 279 pages.

PCT International Preliminary Report on Patentability for International Application No. PCT/EP2017/078403, dated May 16, 2019, 15 pages.

Chinese Search Results dated Apr. 2, 2021, 1 page.

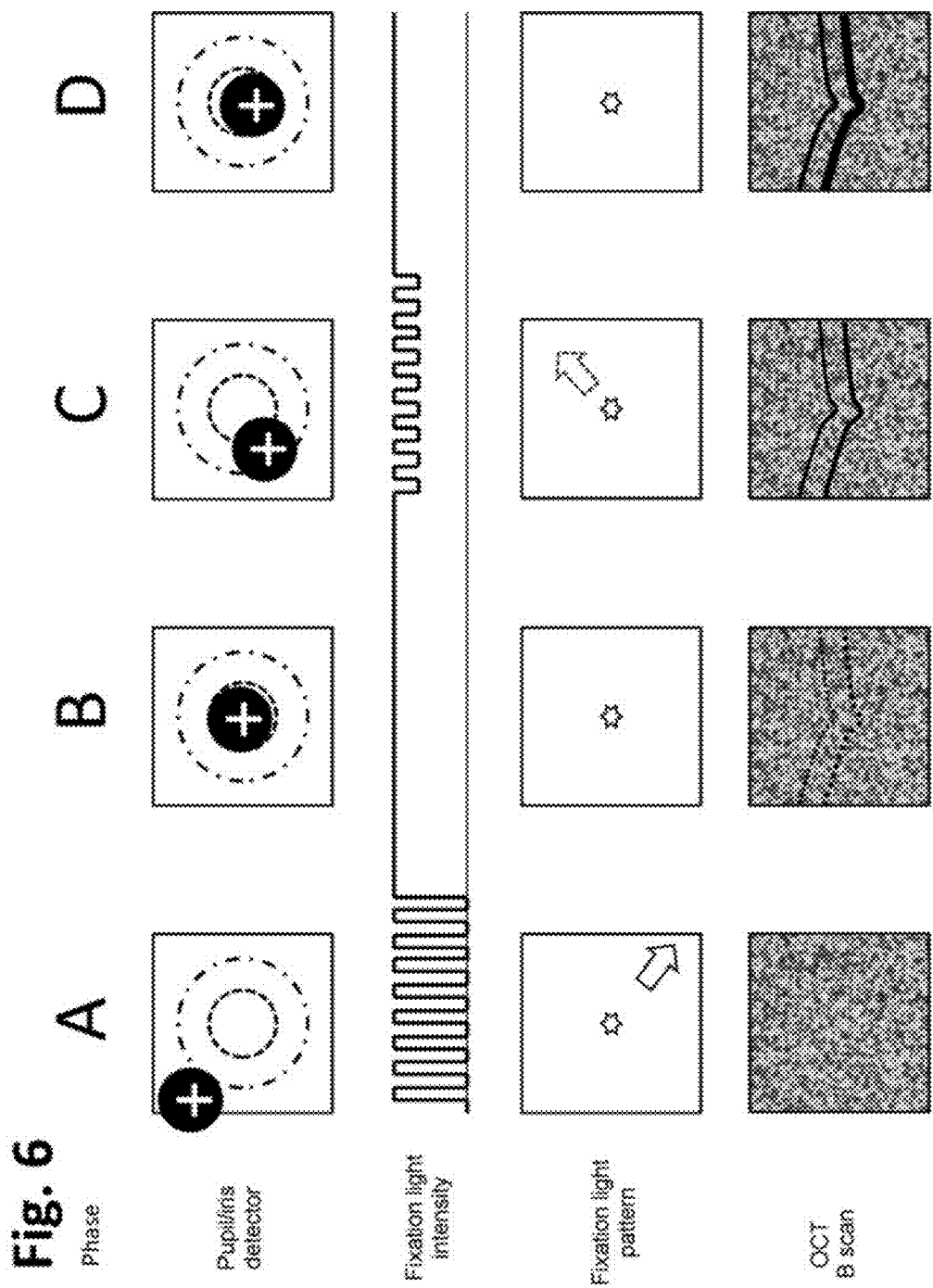

METHOD FOR SELF-EXAMINATION OF AN EYE AND OPHTHALMOLOGICAL SELF-EXAMINATION APPARATUS

RELATED APPLICATIONS

This application is a National Phase entry of PCT Application No. PCT/EP2017/078403 filed Nov. 7, 2017, which application claims the benefit of priority to DE Application No. 10 2016 121 246.6, filed Nov. 7, 2016, the entire disclosures of which are incorporated herein by reference.

The invention relates to a method for examining an eye of a patient by means of an ophthalmological apparatus, which has a front optical unit with an optical axis, the patient positioning the ophthalmological apparatus in relation to the eye and examining the eye. The invention also relates to an ophthalmological apparatus for examining an eye of a patient, which comprises an examination device for examining the eye, which has a front optical unit with an optical axis.

The invention lies in the field of ophthalmological diagnosis, in particular by means of Optical Coherence Tomography (OCT). OCT is an optical method for non-invasively measuring the morphology of the retina (also known as the fundus or fundus oculi). OCT measurements are used to obtain a visible representation of pathological changes of the retina, such as for example AMD (Age-related Macular Degeneration), DME (Diabetic Macular Edema) or RVO (Retinal Vein Occlusion). OCT measurements are usually carried out and assessed by ophthalmologists or specialist ophthalmological personnel. This involves the patient looking into the OCT measuring instrument while the ophthalmologist or other specially trained person performs the alignment of the OCT measuring instrument with respect to the patient and the necessary settings on the OCT measuring instrument.

Among the treatments for disorders of the retina (for example AMD, DME and RVO) are the use of anti-VEGF preparations [VEGF=Vascular Endothelial Growth Factor (signal proteins that stimulate the new formation of blood vessels)]. For optimum therapy, according to the recommendation of the Deutsche Ophthalmologische Gesellschaft (DOG) [German ophthalmological association], the anti-VEGF preparations are injected into the eye specifically whenever at least one of the following clinical findings is obtained: The presence of subretinal fluid, persistence or increase of a diffuse retinal thickening, increase of intraretinal cystoid fluid spaces or increase of a serous pigment epithelial detachment.

Patients in which the aforementioned retinal disorders have been diagnosed, and which are to be treated correspondingly, are usually instructed to attend an ophthalmological practice at intervals of at least a month. An OCT measurement is carried out there and, depending on the finding, an anti-VEGF injection is performed. The problem here is that two undesired cases may occur:

a) The pathological retinal changes have progressed to such extent within the interval of at least a month that the anti-VEGF injection would be performed too late. In this case, irrevocable damage to the patient's retina could occur.

b) There have been no significant retinal changes within the interval of at least a month. In this case, the patient has needlessly attended the ophthalmological practice, with the corresponding expenditure of time and cost this involves for all concerned.

Numerous OCT measuring methods are known from the literature, for example from "Optical Coherence Tomography—Technology and Applications", Editors: Wolfgang Drexler, James G. Fujimoto, Springer International Publishing AG, ISBN: 978-3-540-77549-2.

The object of the invention is to provide a method and an ophthalmological apparatus by means of which a patient can carry out a pre-examination of an eye without medical assistance.

The invention is defined in claims 1 and 13. The dependent claims describe preferred developments of the invention.

An imaging, ophthalmological instrument produces the best image quality when the pupil of the instrument lies at the same spatial location as the pupil of the eye of the patient being examined. For this purpose, the center points of the two pupils should lie at the same location, both in the direction of the optical axis and perpendicularly thereto, i.e. laterally.

The aim of the invention is to achieve this spatial overlapping of the pupils by involving the patient.

A basic precondition for using the invention is that the patient is capable of perceiving a fixation light pattern and fixing on it. During fixation, the person tries to intuitively align himself or herself in such a way that a sharp image of the fixation light pattern is formed on the fovea, that is to say the region of the retina that provides the clearest vision. In patients with visual impairments (for example with AMD), the region of the retina that provides the clearest vision may also lie outside the center of the fovea. In any event, the visual axis of the patient is established by this fixation. Not established by this fixation, on the other hand, is the position of the pupil of the eye in relation to the pupil of the instrument. Although the patient can orient itself approximately on the basis of the vignetting of the fixation light pattern, this is generally not sufficient for an optimum image quality of the ophthalmological measurement. With the aid of the invention, this deficiency is overcome.

In the case of a method for examining an eye of a patient by the patient itself, by means of an ophthalmological apparatus which has a front optical unit with an optical axis, several pupil positioning steps are carried out. In a step a), the patient positions the ophthalmological apparatus in relation to its eye. In a step b1), a measure of a lateral and/or axial deviation of a position of the pupil of the eye from the pupil of the apparatus is determined. In a step b2), depending on the measure of the deviation, a pupil position correction signal, which indicates a direction and/or a degree of the deviation, is generated and output to the patient. On the basis of the pupil position correction signal, the patient can perform a repositioning of the ophthalmological apparatus with a smaller deviation. In a step b3), steps b1) and b2) are repeated until the measure of the deviation lies below a prescribed limit value. In a step c1), it is checked whether a focal plane of the ophthalmological apparatus lies in a prescribed region. In a step c2), if the focal plane does not lie in the prescribed region of the eye, a focus signal with the aid of which the patient can bring the focal plane into the prescribed region is generated and output to the patient. Alternatively, the focal plane is set by means of autofocus. In a step c3), steps c1) and c2) are repeated until the focal plane lies in the prescribed region. After completion of steps b) to c), in a step d) the eye is examined.

An ophthalmological apparatus for examining an eye of a patient by the patient itself has an examination device for examining the eye which comprises a front optical unit with an optical axis. A positioning device of the ophthalmological apparatus records a measure of a lateral and/or axial deviation of a position of the pupil of the eye from the pupil of the apparatus and, depending on the measure of the deviation, generates a pupil position correction signal, which indicates a direction and/or a degree of the deviation. The positioning device outputs the pupil position correction signal to the patient, who can on the basis of the pupil position correction signal perform a repositioning of the ophthalmological apparatus with a smaller deviation. A focal plane adjusting device of the ophthalmological apparatus records whether a focal plane of the ophthalmological apparatus lies in a prescribed region. If the focal plane does not lie in the prescribed region, the focal axis setting device generates a focus signal, with the aid of which the patient can bring the focal planes into the prescribed region, and outputs the focus signal to the patient. Alternatively, the focal plane adjusting device sets the focal plane by means of autofocus.

In ophthalmological examinations of the eye, it is usually necessary to set the ophthalmological apparatus and the eye in relation to one another, in particular with regard to the alignment of the ophthalmological apparatus with respect to a pupil of the eye. The accuracy of the setting has an effect on the quality of the examination. In conventional examinations, the positioning and alignment of the ophthalmological apparatus with respect to the eye is performed by the physician or medically trained personnel. An advantage of said method and said apparatus is that the patient itself can perform the positioning and alignment of its eye in relation to the ophthalmological apparatus. The positioning of the eye in relation to the ophthalmological apparatus can be achieved by a changing of the position of the eye and/or of the ophthalmological apparatus. The ophthalmological apparatus or the method assists the patient in doing this. In particular, no other person is necessary. It is consequently possible that the patient can perform a pre-examination of its eye itself. If the patient is in possession of such an ophthalmological apparatus, it can carry out pre-examinations at home, whereby unnecessary examinations at the physician's practice can be avoided. This saves time and costs.

The ophthalmological apparatus may be designed for generating OCT images of the retina. For example, the examination device is an OCT measuring device. Furthermore, the examination device in the form of an OCT measuring device may not only form images of the retina, but alternatively or in addition form images of a front portion of the eye or biometrically measure the eye. Also, the ophthalmological apparatus may be designed as a fundus camera, a keratometer and/or topograph, i.e. the examination device of the ophthalmological apparatus may comprise a fundus camera, a keratometer and/or a topograph.

The ophthalmological apparatus has for example a handle, a shaft or the like, by means of which the patient can hold the ophthalmological apparatus in order to position it in front of its eye. Alternatively or in addition, the ophthalmological apparatus may be designed in such a way that it can be placed on an underlying surface, such as a table or shelf, the patient positioning the eye in front of the ophthalmological apparatus. For this purpose, a standing leg or a tripod may be provided. In this case, the ophthalmological apparatus is supported and the patient positions its eye in front of the ophthalmological apparatus. The handle, the shaft, the standing leg or the tripod may be attached to the housing of the ophthalmological apparatus.

The examination device makes it possible in particular to carry out an optical examination method on the eye. The examination device optionally has an examination beam path, by which radiation passes to the eye and/or radiation reflected or emitted by the eye for the examination of the eye passes to a corresponding detector. The examination beam path contains the front optical unit, which defines the optical axis. The front optical unit is for example that optical unit of the examination beam path that lies closest to the eye. The pupil of the eye must be aligned to be in line with the pupil of the front optical unit. Steps b1) to b3) are concerned with this alignment. In a prior step b0), the patient may be optically and/or haptically and/or acoustically requested to begin aligning the pupil of its eye with the pupil of the apparatus, or vice versa. The positioning device is then designed to generate optical and/or haptic and/or acoustic signals and to output them by means of a signal generating device, a voice output being possible for example as the acoustic signal.

In step b1), a measure of a lateral and/or axial deviation of a pupil of the eye from the pupil of the apparatus is determined. The deviation of the pupil of the eye from the pupil of the apparatus may relate to a lateral offset, i.e. transversely in relation to the optical axis, and/or to an axial offset, i.e. longitudinally in relation to an optical axis, or also comprise a 3D deviation vector. The measure of the deviation quantifies the deviation. It can be determined in many ways, and for example also be recorded without determining the deviation itself, i.e. the deviation is recorded indirectly.

The measure of the deviation is used to generate the pupil correction signal, which assists the patient in reducing the deviation. For example, the pupil correction signal is inverse to a degree of the deviation. The pupil correction signal may comprise optical and/or haptic and/or acoustic signals. For example, a degree of the deviation may be indicated by way of the tone pitch or a repetition frequency of an acoustic signal: the closer the pupil of the apparatus lies to the pupil of the eye, the higher the repetition frequency of the acoustic signal may be. By analogy, a vibration signal may also represent a pupil correction signal by variation of the vibration frequency. Furthermore, it is possible that there is displayed to the patient an arrow and/or a forward/backward signal, the direction and/or length of which indicates the direction and/or the degree of the deviation. The positioning device may comprise a display, a loudspeaker or a vibration device.

Once the measurement of the measure of the deviation, the generation of the pupil correction signal and the realignment of the pupil of the eye with respect to the pupil of the apparatus by the patient on the basis of the pupil correction signal have taken place, it is checked whether the measure of the deviation lies below a prescribed limit value. This limit value may for example correspond to a maximum, lateral/axial or three-dimensionally indicated offset, the undershooting of which is necessary for an examination of a prescribed quality. In particular, a lateral or axial offset may lie in a radius of acceptance, so that it may also be a prescribed limit value. It is also possible that two different limit values are indicated axially and/or laterally, a first prescribed limit value representing a minimum condition for being able to carry out an examination of the eye, and a second prescribed limit value indicating a condition under which examinations of increased quality are produced. For example, the prescribed lateral limit value for the positioning of the pupil of the eye with respect to the pupil of the apparatus may be a radius of acceptance, the region within the radius of acceptance indicating positions of the pupil of the eye with respect to the pupil of the apparatus.

Optionally, during step d) it is monitored whether the measure of the deviation remains below a prescribed limit value and, if the limit value is overshot, the examination is aborted in step d) and/or an error signal is generated and output to the patient.

In steps c1) to c3), the focal plane of the ophthalmological apparatus, and in particular of the examination device, is set. This may also be referred to as focusing. If the focal plane has not been set correctly, it may happen that, even with a perfect lateral adjustment, a beam generated by the ophthalmological apparatus does not completely pass the pupil, but is vignetted by the iris, since the beam has too great a diameter in the pupil. By changing the focal plane, this undesired effect can be reduced or eliminated. Furthermore, in this way a sharpness of the imaging of the eye can be optimized.

In an optional step c0), the focal plane adjusting device generates a request signal and outputs it for example with the aid of the already mentioned signal generating device. The request signal requests the patient to set the focal plane. In step c1), it is checked whether the focal plane of the ophthalmological apparatus lies in a prescribed region, the prescribed region comprising for example the depth-of-field region in which the examination is possible. It should be arranged in such a way that it coincides in the direction of the depth for example with the retina to be measured. In this case, an image of the retina can for example be optimally formed by means of the OCT measurement.

In step c2), it is checked whether the focal plane lies in the prescribed region, for example in that a test examination is carried out and its result is checked as to whether or not the focal plane lies in the prescribed region. If, for example, the depth-of-field region of an OCT measurement does not include the retina, no image of the retina can be formed in the test OCT examination. With optical imaging methods, it can be checked whether the test image generated has a certain sharpness. If there is not a sufficient focusing state, a focus signal is generated and output to the patient, for example by means of the signal generating device. The focus signal may be a haptic and/or acoustic and/or optical signal. For this purpose, the focal plane adjusting device may have a display, a loudspeaker and/or a vibration device. It is also possible that the positioning device and the focal plane adjusting device share a device for generating the acoustic, optical and/or haptic signal, for example the signal generating device.

On the basis of the focus signal, the patient can move the focal plane in the corresponding direction, so that it lies in the prescribed region. For this purpose, an adjustable optical unit in the examination beam path may for example adjust the focal plane. The adjustment may take place manually, for example in that the patient changes lenses or lens systems by way of a manual drive or the actuation of a motor drive. The focus signal may for example indicate in which direction the focal plane must be shifted. Furthermore, the focal plane can also be adjusted by displaying to the patient an image that appears sharp when the focal plane lies in the prescribed region. This is particularly intuitive in terms of operation, because the patient simply has to make the image sharp. The focus signal may comprise the representation of such an image, so that the patient moves the focal plane into the prescribed region by making this image sharp. In addition, it is possible that the focal plane adjusting device has an autofocusing device, which automatically moves the focal plane into the prescribed region. Autofocusing devices are known from the prior art and can be used for activating the focal plane adjusting device.

In step c3), the process of checking whether the focal plane lies in the prescribed region and readjusting the focal plane is repeated until the focal plane lies in the prescribed region. When using an autofocusing device, it may be that there is no need for renewed checking whether the focal plane lies in the prescribed region. Optionally, during the examination it may be checked in step d) whether the focal plane still lies in the prescribed region and, if this is no longer the case, the examination may be aborted or an error signal generated and output to the patient.

In step d), the measurement is performed, in that both the lateral and/or axial alignment (positioning of the pupil of the apparatus with respect to the pupil of the eye) satisfies a prescribed condition and the focusing (focal plane in the prescribed region) is carried out. Steps c1) to c3) may also be performed before steps b1) to b3). Optionally, the sequence of setting the focal plane and aligning and positioning the pupil of the eye with respect to the pupil of the apparatus depends on the optical examination method that is used.

In an optional development for recording the measure of the deviation, it is provided that an image of the iris of the eye is formed on an iris detector by means of a first beam path, the position of the iris is recorded and this is used to determine the position of the pupil of the eye in order to determine the measure of the deviation. The first beam path contains in particular the front optical unit. The iris detector may comprise a camera by means of which the imaging of the iris can be converted into electrical signals. The iris detector and the first beam path may be part of the positioning device. By the imaging of the iris on the iris detector, the pupil of the eye can also be recorded, because the iris delimits the pupil. The imaging of the iris on the iris detector can then be used to record the position of the iris, and consequently of the pupil, axially and/or laterally.

In an alternative or additional development of the positioning device, an image of radiation reflected at a cornea of the eye is formed on a spatially resolving detector and a position of the cornea reflection on the detector is determined, the position of the reflection on the detector representing a measure of the deviation. The position and alignment of the cornea can be used to determine the position of the pupil of the eye. Depending on the position and alignment of the cornea, radiation reflected at the cornea falls onto different regions of the iris detector. In this way, the position of the pupil of the eye, and consequently a measure of the deviation, can be determined from the reflection, for example with the aid of a computer program or a control device which comprises for example a microprocessor. The relationship between the position of the pupil of the eye and the location of the reflection on the iris detector can be determined by a calibrating measurement.

To be able to form a better image of the iris and/or better generate a reflection at the cornea, it is preferred in a development to illuminate the eye. Optionally, the iris is illuminated with an iris illumination source, a radiation generated by the iris illumination source being coupled into the first beam path by means of a first beam splitter and/or the iris illumination source being arranged between the eye and the front optical unit. The iris illumination source has for example a light-emitting diode, an LED or a laser. The wavelength range for the radiation generated by the iris illumination source lies in particular in the region of 700 to 800 nm, since in this region the sensitivity of the human eye is relatively low, so that no appreciable glare effects are to be expected.

The radiation of the iris illumination source is for example coupled into the first beam path with the aid of a beam splitter, it being possible for the beam splitter to comprise a 50% beam splitter. The beam splitter and the iris illumination source may be elements of the positioning device. The arrangement of the iris illumination source of which the radiation is coupled into the first beam path by way of the beam splitter may be located in the housing of the ophthalmological apparatus and/or of the positioning device, so that a compact type of construction of the ophthalmological apparatus is achieved. Such an arrangement has the advantage that the illumination of the iris takes place parallel to the optical axis, whereby reflections at the cornea can be generated particularly well. It is also possible to arrange the iris illumination source between the front optical unit and the eye, for example the iris illumination source comprises a number of light sources which are arranged distributed around the optical axis, for example as a ring of multiple light sources, for example LEDs. This variant has the advantage that no beam splitter has to be arranged in the first beam path, so that the power of the radiation reflected by the cornea and/or the iris can be lower, since no losses occur at the beam splitter, and at the same time a high-contrast imaging of the iris and/or of the reflection at the cornea is obtained.

In a preferred development, the ophthalmological apparatus serves for examination of the retina by means of OCT images. Optionally, the ophthalmological apparatus comprises an OCT measuring device with an OCT beam source and an OCT detector, and step d) comprises the generation of an OCT image. The OCT measuring device may be part of the examination device. The OCT measuring device may be a point-scanning, line-scanning or non-scanning (known as wide-field or full-field OCT) OCT measuring device. In the case of the point-scanning OCT measuring device, it may be an arrangement in which the retina is scanned simultaneously with numerous measuring points. The OCT measuring device may be designed as a free-beam optical unit or as a fiber-based system. Combinations of free-beam optics and fiber optics are likewise possible. Preferred is an OCT measuring device that operates on the spectral domain principle (SD-OCT) or the swept source principle (SS-OCT). OCT measuring devices that operate on the time domain principle (TD-OCT) can also be used. Depending on the design of the OCT measuring device, the OCT detector may be an area scan camera, a line scan camera or a non-spatially-resolving detector. In order to eliminate temporal fluctuations of the OCT signal originating from the OCT radiation source, multiple OCT detectors may also be used, for example for a balanced detection. The radiation generated by the OCT radiation source lies in particular in the infrared range.

In a preferred development of the OCT measuring device, an OCT beam that is generated by the OCT radiation source is guided via the examination beam path to the retina of the eye, a radiation power of a reflection of the OCT beam at the retina being measured by the OCT detector and taken as a measure of the deviation. The examination beam path optionally has the front optical unit. For example, parts of the examination beam path and of the first beam path may coincide, OCT radiation of the examination beam path or radiation of the first beam path being coupled into the first beam path or into the examination beam path by way of a beam splitter, such as for example a dichroic mirror. The examination beam path also has an OCT beam splitter, which couples the radiation of the OCT beam source into the examination beam path or couples radiation reflected by the retina out of the examination beam path onto the OCT detector. This embodiment serves for determining the alignment of the pupil of the eye on the basis of the reflection of the OCT beam at the retina. With a correct alignment and positioning of the pupil of the eye with respect to the pupil of the apparatus, a particularly great amount of radiation is reflected by the retina onto the OCT detector, so that the measured radiation power is particularly high. This applies in a favorable way both to the lateral positioning and to the axial positioning. The radiation power recorded by the OCT detector consequently represents a measure simultaneously of the lateral deviation and the axial deviation of the position of the pupil of the eye from the position of the pupil of the apparatus. The prescribed limit value may be determined by reference measurements. In particular, the radiation power detected by the OCT detector is at a maximum when no OCT radiation is cut off at the iris. In the case of this variant for determining the measure of the deviation, optionally no interference effects are used as in the case of conventional OCT measurements. It is optionally ensured by confocal suppression that the OCT radiation that falls on the iris cannot reach the OCT detector, for example through a pinhole in the examination beam path. Furthermore, the radiation power of OCT radiation reflected at the cornea may be lower than that used in the OCT imaging. In particular, for this purpose the radiation of an OCT reference beam path may be blocked so as not to reach the OCT detector. A shutter which blocks the reference beam path of the OCT measuring device during the determination of the measure of the deviation may be used for this. If no shutter is provided, it is preferred that the OCT radiation source is designed to be able to provide radiation with lower intensity for the determination of the measure of the deviation and radiation with higher intensity for the generation of an OCT image. The OCT detector has in this case a dynamic range adapted thereto.

Additionally or alternatively, it is provided that an OCT beam that is generated by the OCT radiation source is guided via the examination beam path to the cornea of the eye, an image of a reflection of the OCT beam at the cornea is formed by means of a beam path on a spatially resolving detector and a position of the reflection on the detector is determined. The position of the reflection on the detector represents a measure of the deviation. The detector may for example be the iris detector described above or some other detector. Optionally, the second beam path likewise comprises the front optical unit. The second beam path and the detector may be part of the positioning device. In the case of this method, the recording of the reflection of the cornea described above is used, the radiation that is reflected at the cornea being provided by the OCT measuring device. Preferably, the second beam path shares optical elements with the examination beam path, a beam splitter which couples out the OCT radiation reflected at the cornea onto the second detector being provided. This beam splitter may be a 50/50 beam splitter.

In a development, it is preferred that in a step e1) it is checked whether a coherence condition for a depth-resolved OCT imaging is satisfied. In a step e2), if the coherence condition is not satisfied, a coherence signal with the aid of which the patient can set the coherence condition is generated and output to the patient, or the coherence condition is set automatically by the OCT measuring device. The coherence signal may indicate a degree of coherence or the degree to which the coherence condition is satisfied. In a step e3), steps e1) and e2) are repeated until the coherence condition is satisfied. The setting of the coherence condition is optional, since the OCT measuring device may also have a preset coherence condition that is sufficient for the usual measurements.

What is meant by the coherence condition is that the interferometric beam paths and optical dispersions are coordinated with one another in such a way that the tissue to be measured, such as for example the retina, lies sufficiently well in the OCT measuring region. This requires for example the setting of optical elements, for example mirrors, retroreflectors, lenses, glass plates or optical fibers, that form part of the OCT measuring device. Manual or motor-assisted adjusting elements, such as for example rotary knobs, which the patient can operate while looking into the ophthalmological apparatus, are possible. The OCT measuring device optionally has motorized drives, with which the aforementioned optical elements can be moved. With such motorized drives, the OCT measuring device can also directly perform the setting of the coherence condition automatically. Furthermore, a mechanical or electromagnetic locking device is optionally provided in order to keep the coherence condition stable. The OCT measuring device may record the coherence condition and store it for later OCT measurements of the same eye of the patient. The adjusting elements may be those adjusting elements that are also used for setting the focusing, i.e. the focal plane. The OCT measuring device has in this case mechanical and/or electronic switches, in order to switch over internally between focusing and setting the coherence condition.

In an optional step e0) preceding step e1), the patient may be requested to set the coherence condition. The check as to whether the coherence condition for a depth-resolved imaging is satisfied may be performed with the aid of an OCT test measurement. A coherence setting device may be provided for this. The coherence setting device optionally determines from the OCT test measurement the depth position of the retina in relation to the OCT measuring region of the OCT measuring device. If there are motorized, optical adjusting elements for setting the coherence condition, the coherence measuring device may set the coherence condition automatically. In the case of a manual setting of the coherence condition by the patient, an optical and/or haptic and/or acoustic coherence signal is generated and output to the patient, for example by means of the signal generating device. The coherence signal informs the patient as to whether the setting of the coherence condition is suitable or must be corrected, and optionally in which direction the correction has to be made. The coherence signal may be obtained as described above by analogy with the generation of the pupil correction signal or the focus signal. In step e3), steps e1) and e2) are repeated until the desired coherence condition is satisfied.

A particularly simple alignment and positioning of the pupil of the eye with respect to the pupil of the apparatus takes place in a preferred development in that a fixation light source for generating a fixation light that is visible for the patient is provided, the pupil correction signal comprising a temporal and/or spatial and/or spectral variation of the fixation light. The fixation light is optionally presented to the patient by using the front optical unit. The fixation light source may for example comprise a display, such as a monitor. For aligning the pupil of the eye, the patient looks at the fixation light. This may already bring about an approximate alignment and positioning of the pupil of the eye in relation to the pupil of the ophthalmological apparatus. A fine adjustment may be performed by the fixation light being varied temporally, for example periodically, spatially or spectrally in such a way that, by this variation, the positioning and alignment of the pupil of the eye in relation to the pupil of the ophthalmological apparatus is improved if the patient complies with the variation of the fixation light or follows the instructions specified by it. The fixation light source may for example display patterns such as a cross, a star, a square, a ring, or a ring with a dot in the center. In this way, suitable alignment of the pupil of the eye is achieved particularly well when the patient intuitively positions itself in relation to the ophthalmological apparatus in such a way that an image of the center of the fixation light pattern is formed on the center of the fovea. The variation of the fixation light is controlled depending on the measure of the deviation, so that the variation then represents the output of the pupil correction signal.

In an optional development, it is preferred that the ophthalmological apparatus has a manually and/or motor-variable headrest, an individual presetting for positioning the ophthalmological apparatus in relation to the eye and/or in relation to the focal plane being stored. The headrest may for example comprise a resting surface for the forehead, nose and/or chin. Each patient has individual anatomical or biometric characteristics that are of significance for the intended examination. These include in particular the visual acuity or the visual defect (in dioptrics), the interpupillary distance, the eye length and the position of the eyes in relation to the forehead, chin or some other surface of the head. Individual instrument parameters can be derived from these characteristics and be preset at the headrest or on the ophthalmological apparatus. These parameters are stored or preset in the positioning device and are retrieved when a patient wishes to perform an examination on itself by means of the ophthalmological apparatus.

For the setting (not only of the headrest but for example also of the focal plane), it is preferred to store setting values and make them retrievable for the patient. In this way it is also possible for several people, for example of a family, to use the same instrument and to retrieve their personal setting. The ophthalmological apparatus may also include magnetic, electronic and/or optical sensors with which the patient is recognized, so that the instrument parameters can be set automatically and without any further action to a specific patient for whom values are stored. This is advantageous if several different people use the ophthalmological apparatus alternately. For example, such instrument parameters may comprise the settings for the headrest, the interpupillary distance and/or the momentary focal plane of the ophthalmological apparatus.

In an optional development, a result of the examination that is generated in step d) is compared with a comparative result of a comparative examination and, on the basis of the comparison, a suggestion as to whether a further examination should be carried out by a physician is output to the patient. This may be carried out by an analysis device. For example, the analysis device investigates on the basis of the OCT measurement whether there are retinal lesions or individual changes of retinal lesions. In the case of retinal lesions, nomogram data of retinal disorders of a large number of patients, which are for example stored in the analysis device, are used to assess present lesions. In the case of individual changes of retinal lesions, earlier OCT measurements of the same patient, which may also be stored in the analysis device, are used to assess individual changes. The analysis device may be realized as a software program, which is in particular suitable for image analysis. The analysis device either issues a recommendation to go to see a physician, or a recommendation not to see a physician. These recommendations may in turn be output to the patient by the signal generating device. However, differentiated information may also be output.

Optional developments of the invention are summarized below in the form of key points, it being possible for the individual elements to be combined with one another in any way desired:

By means of manual or motorized adjusting elements, the patient additionally adopts the setting of an interferometric delay for producing the coherence condition for a depth-resolved OCT measurement of the retina.

The patient obtains from the coherence setting device optical and/or acoustic and/or haptic information about satisfying the coherence condition for a depth-resolved OCT measurement of the retina.

The coherence setting device determines on the basis of at least one OCT depth cross section (B scan) whether the coherence condition for a depth-resolved OCT measurement of the retina is satisfied.

The ophthalmological apparatus provides the patient with optical information by means of temporal and/or spatial and/or spectral variations of a fixation light as a pupil correction signal.

The ophthalmological apparatus provides the patient with acoustic information by means of a voice output as a pupil correction signal.

The ophthalmological apparatus provides the patient with acoustic information by means of variation of the volume and/or tone pitch and/or tone duration as a pupil correction signal.

The ophthalmological apparatus provides the patient with haptic information by means of vibrational actions.

The ophthalmological apparatus indicates to the patient optically and/or acoustically and/or haptically the successful or unsuccessful completion of the depth-resolved measurement of the retina.

The ophthalmological apparatus has a voice output.

The ophthalmological apparatus has an individualized headrest for the pre-alignment of the patient in relation to the ophthalmological apparatus.

The ophthalmological apparatus has an apparatus that can be displaced or tilted or rotated manually or in a motorized manner for changing between the left eye and the right eye.

After successful preparation, the examination device measures at least one OCT depth cross section (B scan) or an OCT volume image (C scan).

An analysis device carries out a spatially resolved layer thickness determination of the retina on the basis of the OCT measurements.

The analysis device carries out a qualitative or quantitative determination of accumulations of fluid in the retina on the basis of the OCT measurements.

The analysis device provides the patient optically and/or acoustically and/or haptically with information about whether on the basis of the depth-resolved measurement of the retina performed the patient should go see a physician.

The ophthalmological apparatus is fastened on a removable tripod.

The positioning device, the focal plane adjusting device, the coherence setting device and the analysis device may comprise microprocessors or be formed as part of a computer.

The positioning device changes the fixation light pattern or patterns on the basis of the pupil/iris detection.

The pupil/iris detection is carried out with one or more radii of acceptance.

The fixation light source generates flashing fixation light patterns, flashing fixation light patterns with variable modulation depth of the intensity, fixation light patterns that provide directional information, multiple fixation light patterns with different brightnesses, multiple fixation light patterns with different colors, fixation light patterns with temporally varying colors, arrow-like fixation light patterns, annular fixation light patterns, bright fixation light patterns on a darker background and/or dark fixation light patterns on a brighter background.

Dichroic beam splitters may be provided for overlaying OCT, fixation-light and iris-illumination radiation.

The iris illumination provides an illumination of the pupil/iris on the optical axis and/or outside the optical axis.

Whenever mention is made here of steps (for example b1) and b2) or c1) and c2) or e1) and e2)) being repeated until a certain state is achieved (for example undershooting a limit value or reaching a prescribed region), it is possible in one development that the method is aborted with an error message if a predetermined number of repeats has been reached. This may optionally be a qualified error message, which indicates which setting attempt (for example position of the pupil or focal plane) failed.

An evaluation and control device, which for example activates the apparatus to perform the method steps mentioned at the beginning, is expedient for the apparatus.

It goes without saying that the aforementioned features and those yet to be explained below can be used not only in the combinations specified but also in other combinations or on their own, without departing from the scope of the present invention.

The invention is explained in even greater detail below for example with reference to the accompanying drawings, which also disclose features essential to the invention. In the figures:

FIG. 6 shows a schematic representation of a pupil correction signal and corresponding effects on an OCT scan.

Figure 1:
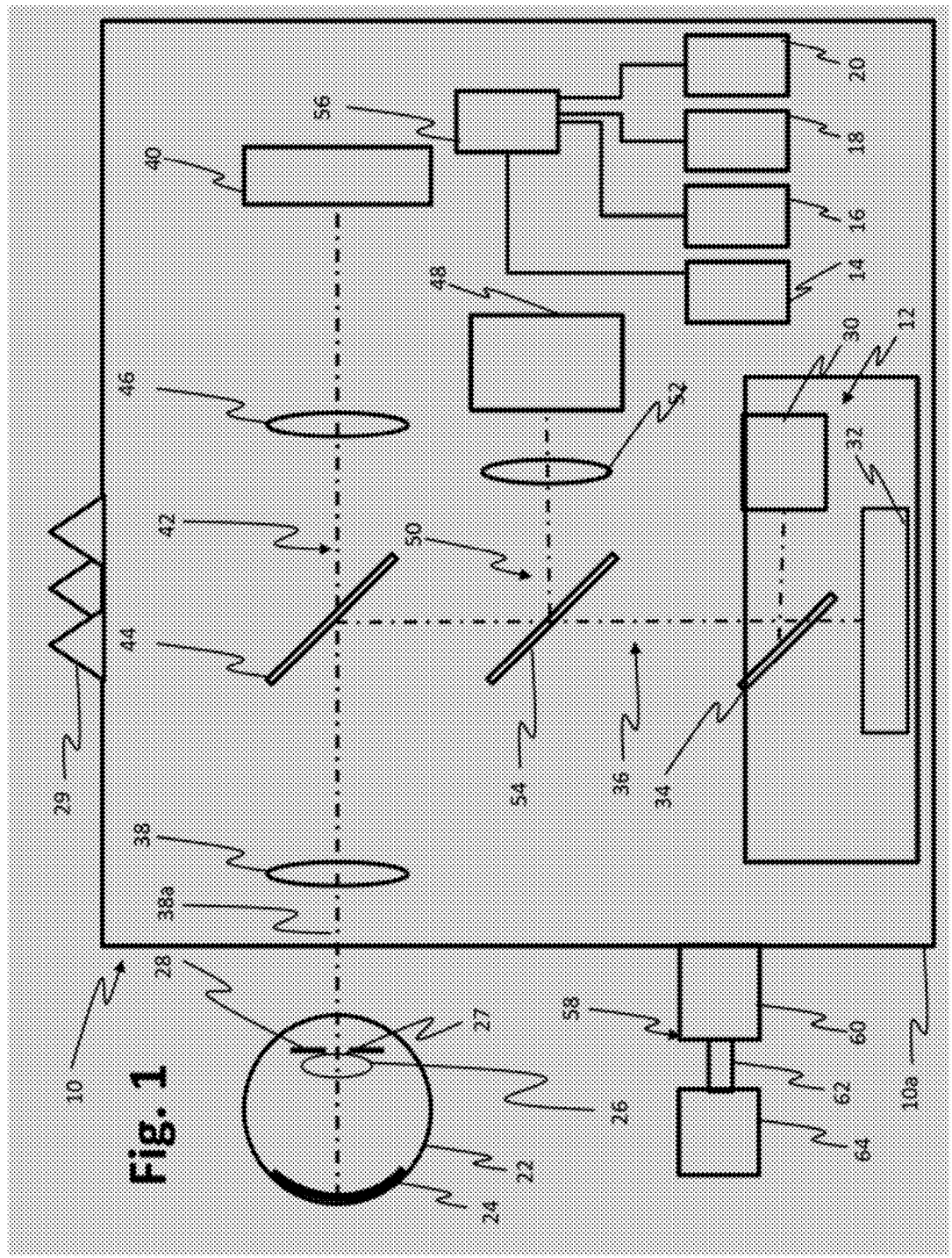
FIG. 1 shows a schematic representation of elements of an ophthalmological apparatus according to a first embodiment.

An ophthalmological apparatus 10, such as that represented in FIG. 1, comprises an examination device 12, a positioning device 14, a focal plane adjusting device 16, a coherence setting device 18 and an analysis device 20. The ophthalmological device 10 serves for the examination of an eye 22 of a patient. The positioning device 14, the focal plane adjusting device 16, the coherence setting device 18 and the analysis device 20 may comprise microprocessors or be formed as part of a computer.

The eye 22 has a retina 24, a lens of the eye 26 and an iris 28. The iris 28 surrounds a pupil of the eye 27. In the embodiment represented, the examination device 12 is an OCT measuring device, by means of which an image of the retina 24 can be formed. However, it is also possible that the examination device 12 that is used for examining the eye 22 comprises instead or in addition a fundus camera, a keratometer or a topograph. The examination device 12 does not have to be restricted to forming an image of the retina 24, but may also form images of other portions and/or tissues of the eye 22 or may biometrically measure the eye 22.

For the examination, the center point of the pupil of the eye 27 should lie at the same place as the center point of the pupil of the ophthalmological apparatus 10. In this case, it is also ensured that the axis of symmetry of the pupil of the apparatus 38a passes through the center of the pupil of the eye 27.

The ophthalmological apparatus 10 has a housing 10a. Arranged in the housing 10a are the examination device 12, the positioning device 14, the focal plane adjusting device 16, the coherence setting device 18, the analysis device 20 and further elements of the ophthalmological apparatus 10 as described below. Elements of the ophthalmological apparatus 10 that are not arranged within the housing 10a are specially indicated below. For example, a tripod 29 by means of which the housing 10a can be positioned on an underlying surface is arranged on the housing 10a. Alternatively or in addition, a handle for holding the ophthalmological apparatus 10 may be attached to the housing 10a. The tripod 29 and/or the handle are not provided inside the housing 10a.

The examination device 12 has an OCT radiation source 30, an OCT detector 32 and an OCT beam splitter 34. The OCT radiation source 30 generates OCT illumination, optionally in the infrared range, by means of which the retina 24 is illuminated. The OCT detector 32 detects OCT illumination reflected by the retina 24 in order to generate an OCT image. The examination device 12 also has a reference arm, which is not shown in the figures. The OCT illumination is passed from the examination device 12 to the eye 22 and the OCT measuring radiation reflected at the retina 24 is passed from the retina 24 to the examination device 12—in each case via an examination beam path 36. The OCT beam splitter 34 couples the OCT illumination provided by the OCT radiation source 30 into the examination beam path 36. However, it is also possible that the OCT beam splitter 34 couples the OCT measuring radiation reflected at the retina 24 out of the examination beam path 36 onto the OCT detector 32. The examination beam path 36 comprises a front optical unit 38, which is that optical unit of the ophthalmological apparatus 10 that lies closest to the eye 22. The front optical unit 38 may comprise one or more lenses; in particular, a focal length of the front optical unit 38 can be set by moving the lenses in relation to one another. Adjusting elements such as rotary knobs may be provided for this. The front optical unit 38 defines an axis of symmetry of the pupil of the apparatus 38a.

The examination device 12 may be a point-scanning, line-scanning or non-scanning (known as wide-field or full-field OCT) OCT measuring device. In the case of the point-scanning examination device 12, it may be an arrangement in which the retina 24 is scanned simultaneously with numerous measuring points. The examination device 12 may be designed using free-beam optics or as a fiber-based system. Combinations of free-beam optics and fiber optics likewise come into consideration. Preferred is an examination device 12 that operates on the spectral domain principle (SD-OCT) or the swept source principle (SS-OCT). Alternatively, an examination device 12 that operates on the time domain principle (TD-OCT) can also be used. Depending on the design of the examination device 12, the OCT detector 32 may be an area scan camera, a line scan camera or a non-spatially-resolving detector. In order to eliminate temporal fluctuations of the OCT signal originating from the OCT radiation source 30, multiple detectors may also be used, for example for a so-called balanced detection.

The ophthalmological apparatus 10 also has a fixation light source 40, which may be designed as a monitor or display. The fixation light source 40 provides a fixation light, which is guided by means of a third beam path 42 to the eye 22, so that the patient can see this fixation light. The third beam path 42 comprises a third beam splitter 44 and a third optical unit 46. The third beam path 42 likewise comprises the front optical unit 38. In particular, an image of the fixation light of the fixation light source 40 is projected into the eye 22 by way of the third optical unit 46 and the front optical unit 38. With the aid of the third beam splitter 44, the fixation light is coupled into the examination beam path 36. The fixation light is preferably light in the visible wavelength range, it being possible for the third beam splitter 44 to be designed as a dichroic mirror. The third optical unit 46 may comprise one or more lenses that can be moved in relation to one another for changing a focus of the third optical unit 46. Adjusting elements such as rotary knobs may be provided for this.

The ophthalmologic apparatus 10 optionally comprises a spatially resolving detector 48. An image of radiation reflected at the cornea of the eye 22 is formed via a second beam path 50 on the detector 48. The second beam path 50 contains a second optical unit 52 and a second beam splitter 54. The second beam splitter 54 couples radiation out of the examination beam path 36 onto the detector 48. The second optical unit 52 may comprise one or more lenses that can be moved in relation to one another for changing a focus of the second optical unit 52. Adjusting elements such as rotary knobs may be provided for this.

Also provided in the ophthalmological apparatus 10 is an optional signal generating device 56, which is data-technologically connected to the positioning device 14, the focal plane adjusting device 16, the coherence setting device 18 and the analysis device 20. The signal generating device 56 may generate haptic, optical and/or acoustic signals, and in particular a pupil correction signal, a focus signal and a coherence signal. The signal generating device 56 may for example comprise a loudspeaker, a display, such as a monitor, and/or a vibration device.

A headrest 58 of the ophthalmological apparatus 10 is attached to the outside of the housing 10a. It has an adjusting device 60, an adjusting element 62 and a headrest surface 64. The adjusting device 60 may for example comprise a locking mechanism or a drive, such as an electric motor, by means of which the adjusting element 62 can be moved. The adjusting element 62 may for example comprise a rod or a linkage. The patient can place its forehead, nose and/or chin against the headrest surface 64, so that the headrest 58 prepositions the eye 22 with respect to the ophthalmological apparatus 10.

The front optical unit 38, the second optical unit 52 and the third optical unit 46 serve for various imaging purposes, to some extent multiple imaging purposes. The front optical unit 38 and the third optical unit 46 bring about the OCT illumination of the eye 22, the formation of an image of the retina 24 on the OCT detective 32 and the formation of an image of the fixation light on the retina 24. The second optical unit 52 forms an image of the OCT measuring radiation reflected by the cornea on the detector 48.

The third beam splitter 44 separates the examination beam path 36 and the third beam path 42, which may also be referred to as the fixation light beam path. It is preferably a dichroic beam splitter, since the OCT radiation typically lies in the infrared range and the fixation light radiation typically lies in the visible spectral range. Reflection and transmission can of course also be changed over, so that the OCT radiation is transmitted at the third beam splitter 44 and the fixation light radiation is reflected. The second beam splitter 54 couples out a component of the OCT measuring radiation that returns to the eye 22 and directs it by way of the second optical unit 52 to the detector 48. Here, too, reflection and transmission may also be changed over, so that the coupled-out OCT measuring radiation component is transmitted at the second beam splitter 54 and the rest is reflected.

Figure 2:
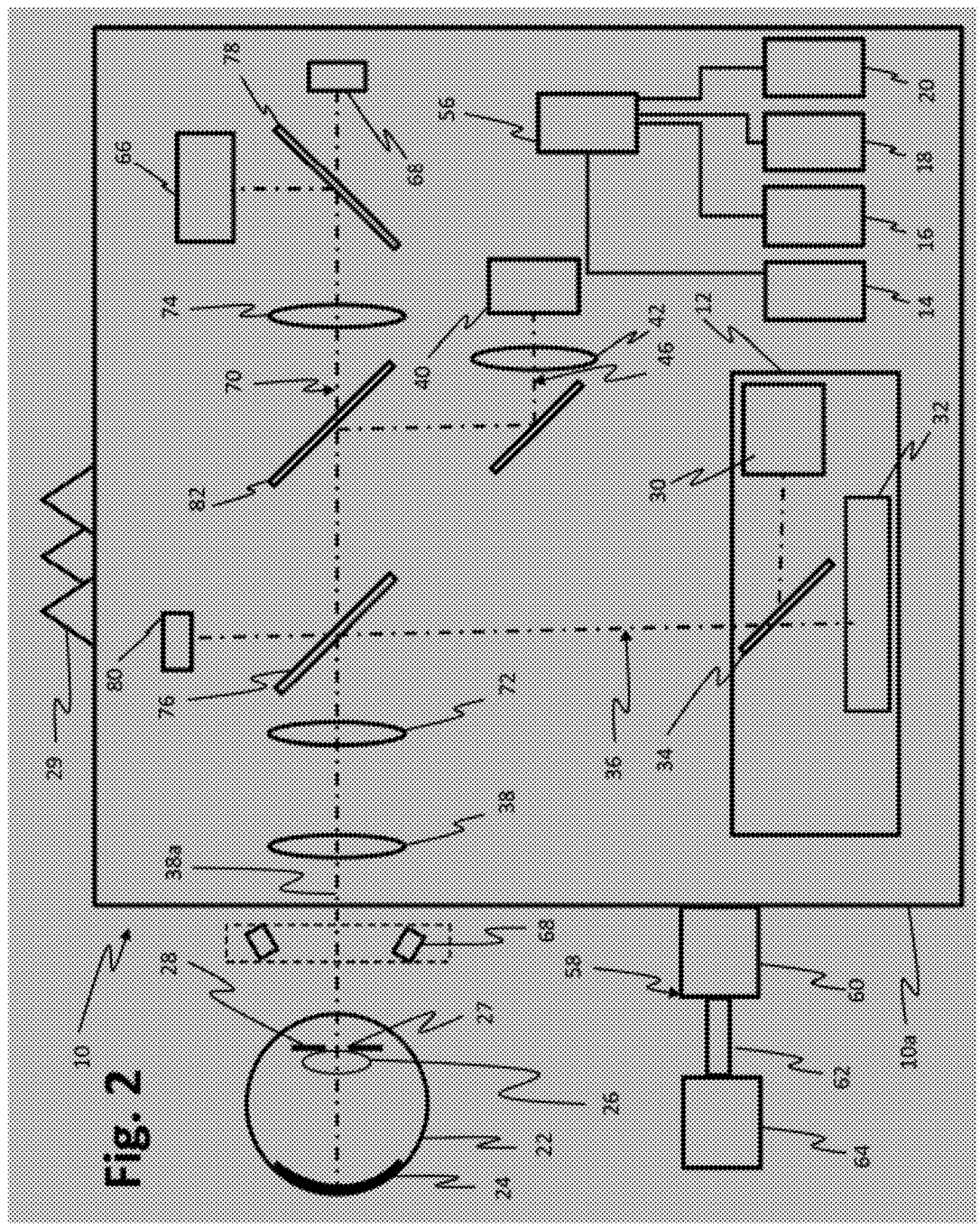
FIG. 2 shows a schematic representation of elements of an ophthalmological apparatus according to a second embodiment.
Figure 3:
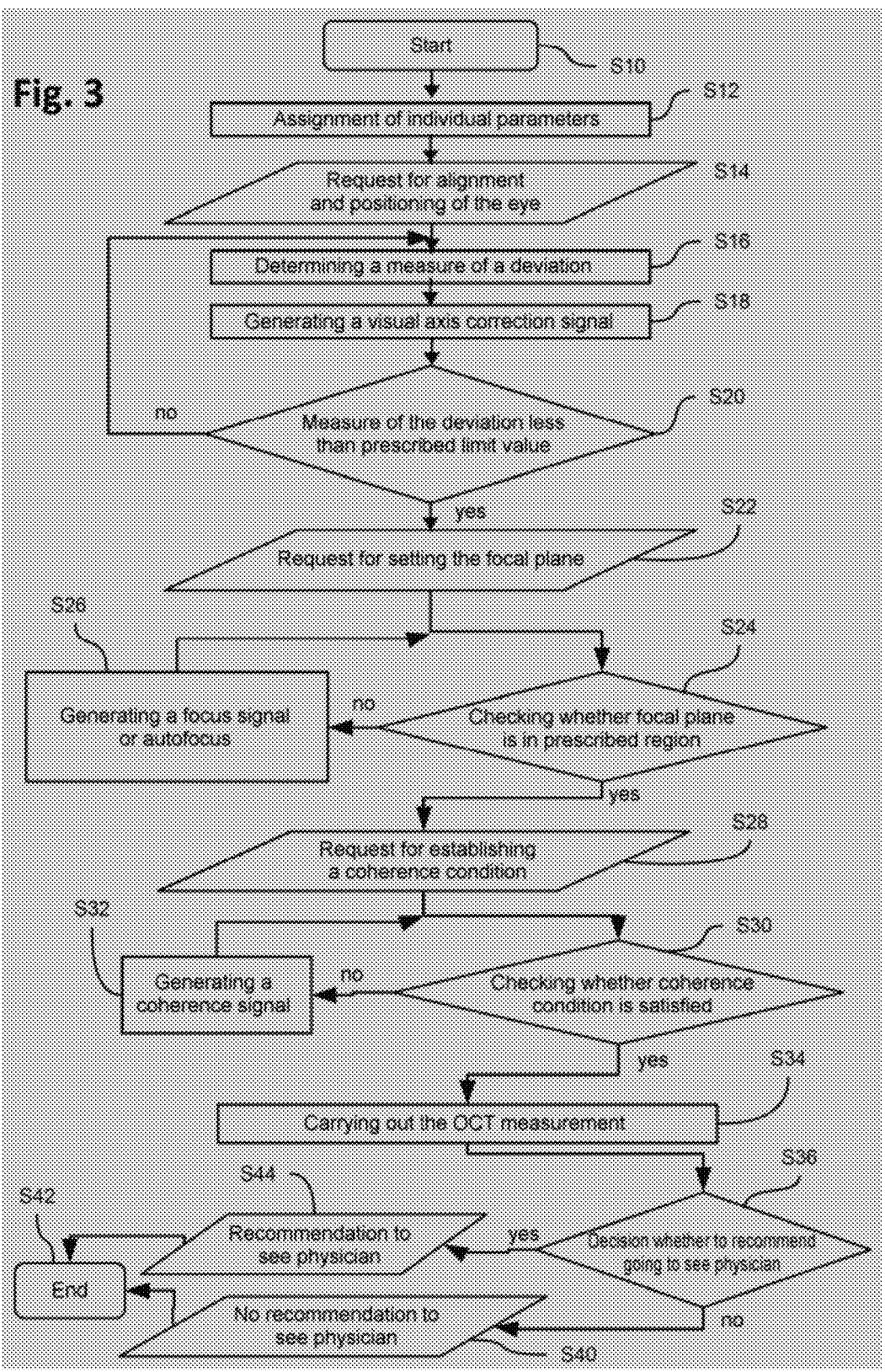
FIG. 3 shows a block diagram for representing essential steps in the examination of an eye of a patient.

FIG. 2 shows a second embodiment of the ophthalmological apparatus 10, which coincides with the ophthalmological apparatus 10 of FIG. 1 apart from the following differences. The ophthalmological apparatus 10 according to FIG. 2 does not have a detector 48 including a second beam path 50. Instead, an iris detector 66 and an iris illumination 68 are optionally provided. An image of the iris 28 is formed via the first beam path 70 on the iris detector 66. The first beam path 70 has a first forward optical unit 72, a first rearward optical unit 74 and a first beam splitter 76. The first forward optical unit 72 and the first rearward optical unit 74 serve for forming an image of the iris 28 on the iris detector 66. The first forward optical unit 72 and the first rearward optical unit 74 may each comprise one or more lenses; in particular, the focus of the first forward optical unit 72 and of the first rearward optical unit 74 is adjustable by moving the lenses in relation to one another, for example with the aid of adjusting elements. The front optical unit 38 forms part of the first beam path 70. By way of the first beam splitter 76, the radiation coming from the iris 28 is coupled out of the examination beam path 36 and directed onto the iris detector 66. The iris detector 66 is a spatially resolving detector, such as for example a camera. The beam splitter 76 may be a dichroic beam splitter. The iris illumination 68 may be designed as a light source which can be coupled by way of an iris beam splitter 78 into the first beam path 70. Furthermore, the iris illumination 68 may be arranged between the eye 22 and the front optical unit 38, optionally outside the housing 10a. The iris illumination 68 may in this embodiment be arranged distributed around an axis of symmetry of the pupil of the apparatus 38a of the front optical unit 38. In this case, the iris illumination 68 may include multiple light sources, such as for example LEDs, which are distributed around the axis of symmetry of the pupil of the apparatus 38a of the front optical unit 38.

With the aid of the first beam splitter 76, part of the OCT illumination is optionally coupled out onto a power monitoring detector 80, which monitors the radiation power of the OCT radiation source 30. In the embodiment of the ophthalmological apparatus 10 that is shown in FIG. 2, the radiation generated by the fixation light source 40, which is guided through the first beam path 42, is coupled by way of a fourth beam splitter 82 into the first beam path 70, and consequently also into the examination beam path 36.

The first beam splitter 76 combines in FIG. 2 the examination beam path 36 with the beam paths of the further components of the ophthalmological apparatus 10. The first beam splitter 76 is optionally designed as a dichroic beam splitter in such a way that it reflects over 90% of the OCT measuring radiation, which generally lies in the infrared spectral range. The first beam splitter 76 transmits a small part (<5%) of the OCT measuring radiation, so that it reaches the power monitoring detector 80. The power monitoring detector 80 is connected to a control and evaluation device (not represented), which ensures that the OCT radiation source 30 is switched off when prescribed limit values for the OCT radiation power are overshot or undershot.

The first beam splitter 76 allows preferably over 90% of radiation that has lower wavelengths than the OCT radiation to be transmitted. This transmitted radiation also includes in particular light that is emitted by the fixation light source 40. The transmitted radiation also includes the illumination and detection radiation for the pupil/iris detection described further below. It should be noted that the first beam splitter 76 may also be designed in such a way that the OCT measuring radiation is transmitted, while the radiation of the fixation light source 40 and of the pupil/iris detection is reflected. In this case, the first beam splitter 76 would reflect a small part (<5%) of the OCT measuring radiation for the power monitoring. The corresponding elements of FIG. 2 would then have to be arranged in a correspondingly changed-over manner.

The fourth beam splitter 82 is optionally designed as a dichroic beam splitter. In the present embodiment, it transmits over 90% of the radiation of the pupil/iris detection, while it reflects over 90% of the radiation of the fixation light source 40. The radiation of the pupil/iris detection preferably lies spectrally between the infrared OCT illumination and the visible radiation of the fixation light source 40. A particularly suitable spectral range for the pupil/iris detection is represented by the wavelength range of 700-800 nm, since in this range the sensitivity of the human eye 22 is relatively low, so that no appreciable glaring effects of the pupil/iris illumination radiation are to be expected. It should be noted that the fourth beam splitter 82 may also be designed in such a way that the fixation light radiation is transmitted, while the radiation of the pupil/iris detection is reflected. The corresponding elements of FIG. 2 would then have to be arranged in a correspondingly changed-over manner.

The iris beam splitter 78 is optionally designed as a simple, non-dichroic 50/50 beam splitter, i.e. the ratio of transmission to reflection is approximately 1. The symbolically represented optical units 38, 72, 74 and 46 serve for beam shaping. Each of these optical units 38, 72, 74 and 46 may comprise one or more lenses and/or mirrors.

A variant for the illumination of the pupil/iris 28 is to radiate the iris illumination 68 through all of the elements of the first beam path 70 that lie on the path to the eye 22. This variant has the advantage that the first beam path 70, which is present in any case, can be used for forming an image of the pupil/iris 28 on the iris detector 66 and the centroid of the illumination lies directly on the axis of symmetry of the pupil of the apparatus 38a of the ophthalmic apparatus 10 Optionally, the position (center) of the pupil/iris 28 or of the cornea reflection of the iris illumination 68 may be determined with the aid of the positioning device 14 and used for the method described here.

An alternative or additional variant for the illumination of the iris 28 is to radiate the iris illumination 68 off-axially (obliquely) onto the pupil/iris 28, so that no or only few optical elements lie between the iris illumination 68 and the eye 22. The iris illumination 68 optionally comprises individual light sources arranged in the manner of a ring. This variant has the advantage that the iris beam splitter 78 can be omitted and less stray light is produced in the optical set-up of the examination device 12 as a whole. Also with this variant, the position of the pupil/iris 28 or the position of a cornea reflection can optionally be used.

For both variants of the iris illumination 68, LEDs are preferred radiation sources. The iris detector 66 optionally comprises a CMOS camera. In the case of the evaluation of cornea reflections, it may also be an optical position sensor (Position Sensitive Detector, PSD).

The ophthalmological apparatus 10 optionally comprises manual or motorized components for setting the fixation (not represented in FIG. 2). The setting may be performed for example by the front optical unit 38 being displaced along the axis of symmetry of the pupil of the apparatus 38a in such a way that the distance between the eye 22 and the front optical unit 38 remains largely constant. This may be performed for example by a rotary wheel, as known from microscopes. This allows individual refractive visual defects to be compensated (dioptric setting). If the fixation light source 40 and the OCT detector 32 lie in conjugate planes, it is sufficient if the patient performs the setting of the fixation in such a way that it sees the fixation light pattern sharply.

A method for examining the eye 22 is described with regard to the ophthalmological apparatus 10 according to FIGS. 1 and 2 on the basis of OCT imaging. However, it is also possible that the method is used in the case of other methods of imaging or methods of examination. The method begins in a step S10. In the step S12 then following, individual parameters of the ophthalmological apparatus 10 personal to the patient carrying out the method are set. These may comprise settings of the headrest 58, in particular the adjusting device 60. Furthermore, it is possible that the focal plane adjusting device 16 sets a focal plane of the ophthalmological apparatus 10 to a value assigned to the patient, in that for example it correspondingly sets the optical units of the examination beam path 36, in particular the front optical unit 38. Every person has individual anatomical or biometric characteristics that are of significance for the intended OCT measurement. These include in particular the visual acuity or the visual defect (in dioptrics), the interpupillary distance, the eye length and the position of the eyes 22 in relation to the forehead rest or some other resting surface of the headrest surface 64. Individual instrument parameters can be derived from these characteristics and be preset on the ophthalmological apparatus 10 as described above. These instrument parameters are for example stored in the focal plane adjusting device 16 and are retrieved when a specific person wishes to perform an OCT measurement on itself. The ophthalmological apparatus 10 may include magnetic, electrical and/or optical sensors with which the patient can be recognized, so that the instrument parameters are individually set automatically and without any further action by the patient. This is advantageous if several different people use the ophthalmological apparatus 10 alternately.

At the beginning of step S14, the patient looks at the fixation light and intuitively directs it eye to it. This establishes the viewing direction of the patient in relation to the axis of symmetry of the pupil of the apparatus 38a. This pre-alignment is assumed to have been performed as a precondition for the further steps.

In step S14, a request signal for the alignment and positioning of the pupil of the eye with respect to the axis of symmetry of the pupil of the apparatus 38a is generated by means of the positioning device 14 and output to the patient by means of the signal generating device 56. This optionally takes place by means of acoustic signals, while acoustic signals are also to be understood in particular as including voice output. For this, the fixation light source 40 may provide a fixation light pattern in the form of a star, a ring, a cross or a combination thereof, the fixation light pattern only being perceptible by the patient as symmetrically bright if there is a good alignment and positioning of the pupil of the eye with respect to the axis of symmetry of the pupil of the apparatus 38a.

In a subsequent step S16, a measure of the deviation between the pupil of the apparatus and the pupil 27 of the eye 22 is determined. Details of this are still to be described below. In a subsequent step S18, a pupil correction signal is generated by the positioning device 14 and output to the patient with the aid of the signal generating device 56 and/or the fixation light source 40. The pupil correction signal may be optical, haptic and/or acoustic; in particular, the pupil correction signal helps the patient to improve the alignment and/or positioning of the pupil of the eye with respect to the axis of symmetry of the pupil of the apparatus 38a. In a subsequent step S20, it is checked whether, after the repositioning, the measure of the deviation is less than the prescribed limit value. This is still to be explained in more detail below on the basis of further examples. If the deviation is not less than the prescribed limit value, the method returns to step S16. If the measure of the deviation is less than the prescribed limit value, the method continues with a step S22.

In step S22, the focal plane adjusting device 16 generates a request for setting the focal plane and outputs it to the patient with the aid of the signal generating device 56. The setting of the focal plane may also be referred to as focusing or fixation and refers to the arrangement of the retina 24 to be measured within a depth-of-field region of the examination device 12. For this, the patient may adjust the optical units of the ophthalmological apparatus 10, in particular the front optical unit 38, in such a way that a focal plane is shifted along the axis of symmetry of the pupil of the apparatus 38a. The fixation is preferably accompanied by sharp perception of the fixation light generated by the fixation light source 40.

In order to obtain a good OCT measuring result, it is checked in a subsequent step S24 whether the focal plane lies in a prescribed region, which optionally coincides with the depth-of-field region for the OCT imaging to be performed. The check whether the focal plane lies in the prescribed region may be determined with the aid of an OCT test measurement or a 2D image of the fundus (i.e. forming an image of the fundus without depth information). To determine this, the focal plane adjusting device 16 determines with the aid of the examination device 12 from the OCT test measurement or the 2D image of the fundus the depth position of the retina 24 in relation to the focal plane of the ophthalmological apparatus 10.

If the focal plane does not lie in the prescribed region, the method continues with a step S26, in which the focal plane adjusting device 16 generates a focus signal and outputs it to the patient with the aid of the signal generating device 56. The focus signal may again be an optical, haptic and/or acoustic signal. For setting the focal plane, the ophthalmological apparatus 10 may have manual or motor-assisted adjusting elements for adjusting the settings of the optical units, in particular the front optical unit 38. These may be in particular rotary knobs, which the patient can operate while looking into the ophthalmological apparatus 10. The adjusting elements may bring about a separate coarse setting and fine setting. Furthermore, a mechanical or electromagnetic locking device is provided in order to keep the fixation state stable. It may be implemented that the focal plane adjusting device 16 records the fixing state and stores it for later OCT measurements of the same patient. The focus signal may indicate in step S26 for example the direction in which the adjusting elements must be turned for changing the focal plane. Alternatively, the ophthalmological apparatus 10, in particular the focal plane adjusting device 16, may have implemented an autofocus, by means of which the focal plane is set automatically. Step S26 is followed by continuing with step S24.

If it was found in step S24 that the focal plane lies in the prescribed region, the method continues with a step S28. Steps S28 to S30 are optional and are carried out by the coherence setting device 18. It should be pointed out at this stage that steps S14 to S20 may also be carried out after steps S22 to S24.

In step S28, the coherence setting device 18 generates a request signal for producing a coherence condition and outputs it to the patient with the aid of the signal generating device 56. What is meant by the coherence condition is that the interferometric beam paths and optical dispersions are coordinated in such a way that the retina 24 to be measured lies in the OCT measuring region. For this, the examination device 12 has optical elements, for example mirrors, retroreflectors, lenses, glass plates and/or optical fibers, which can be moved by the coherence setting device 18 by means of drives or manually. If motorized adjusting elements are present, the coherence setting device 18 can perform the setting of the coherence condition automatically. The request for setting the coherence conditions in step S28 can then be omitted. If, in a simplified and low-complexity configuration, the motorized adjusting elements for setting the coherence condition are to be omitted, it may however also be advantageous that the patient adjusts the optical elements manually.

In a subsequent step S30, it is checked whether the requested coherence condition is satisfied. For this, the examination device 12 may carry out an OCT test measurement and determine from it the depth position of the retina 24 in relation to the OCT measuring region of the examination device 12. If the coherence condition is not satisfied, in a step S32 the coherence setting device 18 generates a coherence signal, which is output to the patient by means of the signal generating device 56. The coherence signal may again comprise an optical, acoustic and/or haptic signal. The coherence condition may be set on the examination device 12, for example by using manual or motor-assisted adjusting elements. These may be rotary knobs, which the patient operates while looking into the ophthalmologic apparatus 10. These adjusting elements may likewise bring about separate coarse setting and fine setting. Mechanical or electromechanical locking devices are also provided, in order to keep the setting of the coherence conditions stable. It may be implemented that the coherence setting device 18 records the setting of the coherence condition and stores it for later OCT measurements of the same patient. The adjusting elements may be those adjusting elements that are used for setting the fixation, i.e. the focal plane. The coherence setting device 18 has in this case mechanical and/or electronic switches, in order to switch over internally between fixation and setting of the coherence condition.

Once step S32 has been carried out and a setting of the coherence condition has taken place, the method continues with step S30. If the coherence condition is met after step S30, the method continues with step S34. This means that, before the beginning of step S34, the essential settings for generating an OCT image of sufficient quality have been successfully completed. In step S34, the examination device 12 generates an OCT image of the retina 24 of the patient. The examination device 12 optionally carries out the OCT measurement autonomously, for example as soon as the positioning device 14, the focal plane adjusting device 16 and the coherence setting device 18 inform the detection device 12 that the setting conditions for an OCT measurement are satisfied. Alternatively, the patient may initiate the OCT measurement itself. The start and end of the OCT measurement may be indicated to the patient by way of optical and/or haptic and/or acoustic signals, which may be generated by the signal generating device 56. In particular, a voice output may also be used for this.

In a subsequent step S36, the analysis device 20 investigates on the basis of the OCT measurement whether there are a) retinal lesions or b) individual changes of retinal lesions. In case a), nomogram data of retinal disorders of a large number of patients, which are for example stored in the analysis device 20, are used to assess present lesions. In case b), earlier OCT measurements of the same patient, which may also be stored in the analysis device 20, are used to assess individual changes. The analysis device 20 may be realized as a software program, which is in particular suitable for image analysis. The analysis device 20 either issues a recommendation to go to see a physician in a step S38 or makes the suggestion not to see a physician in a step S40. These indications may in turn be output to the patient by the signal generating device 56. However, differentiated information may also be output. Following that, the method ends in step S42. For the purpose of OCT image generation, OCT illumination is radiated from the examination device 12 into the eye 22, and radiation that is scattered back at the retina 24 is detected by the OCT detector 32 as OCT measuring radiation. Both types of radiation are referred to here together by the term "OCT radiation".

Figure 4:
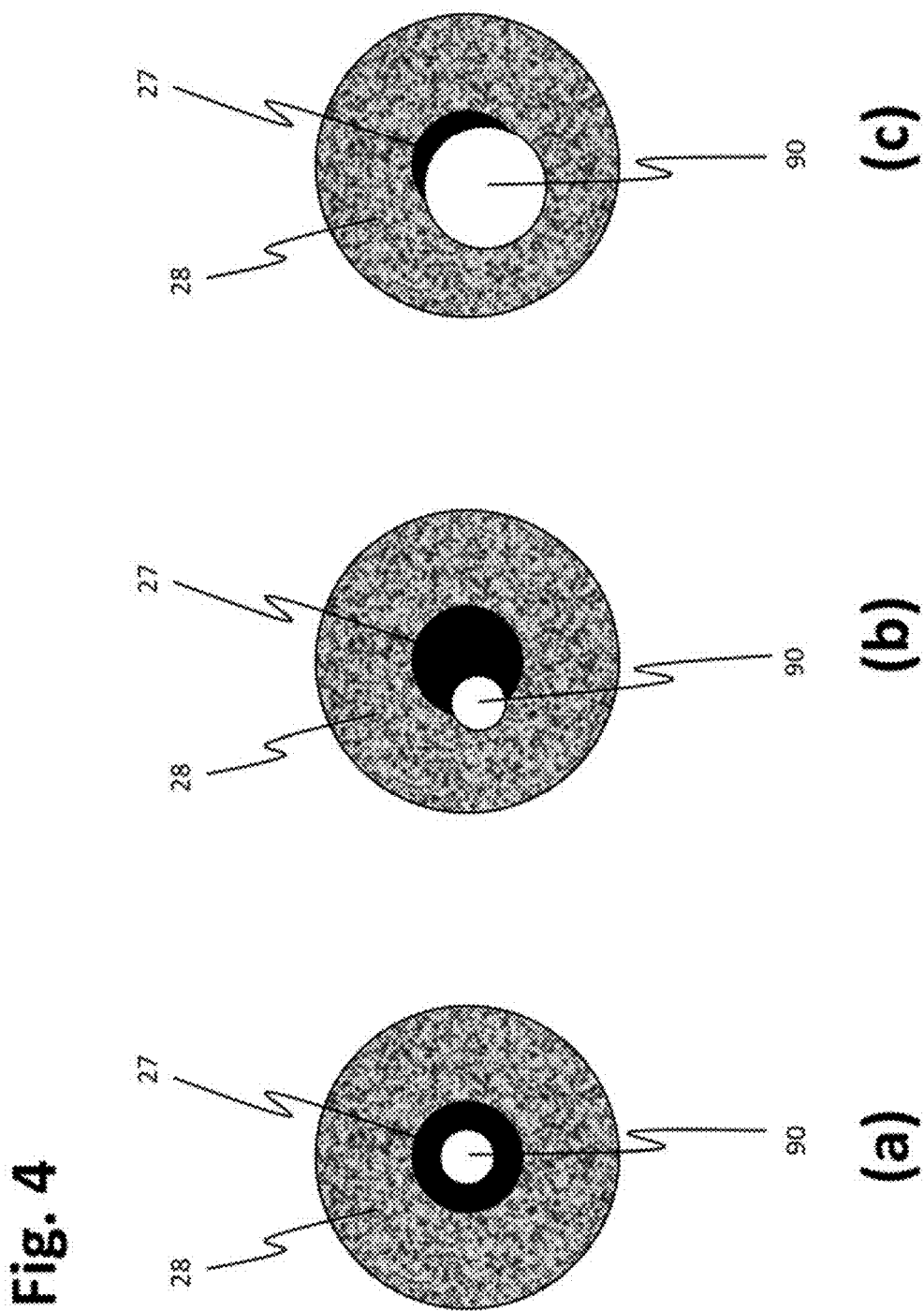
FIG. 4 shows an arrangement of an OCT beam with respect to an eye of the patient in the plane of the pupil of the eye.

FIG. 4 schematically shows the iris 28, which encloses the pupil of the eye 27. Also depicted in the cross section is an OCT illumination 90, which is generated by the OCT radiation source 30. The OCT illumination 90 is shown here as round, but may also be of any other cross section, in particular elliptical, linear, rectangular or annular. In FIG. 4(a), the OCT illumination 90 is aligned optimally, so that no components (or the smallest possible components) of the OCT illumination 90 fall on the iris 28; the axis of symmetry of the pupil of the apparatus 38a and the pupil of the eye coincide with one another. In FIG. 4(b), on the other hand, the OCT illumination has been shifted laterally, so that parts of the OCT illumination 90 impinge on the iris 28, and consequently do not reach the retina 24; the OCT measuring radiation passing in the opposite direction has a similar effect. The axis of symmetry of the pupil of the apparatus 38a is offset with respect to the pupil of the eye 27. In FIG. 4(c), in addition to the lateral misalignment, a false axial positioning of the pupil of the eye 27 is also indicated. In this case, the pupil of the ophthalmological apparatus 10 does not lie in the plane of the pupil of the eye 27 of the eye 22. If the diameter of the OCT illumination 90 is then greater than the pupil of the eye 27 of the eye 22, it may happen that OCT radiation undesirably falls on the iris 28 even when there is no lateral offset.

In a variant, step S16 of the OCT detector 32, which forms part of the examination device 12, is used. The OCT detector 32 serves primarily for generating an OCT image and is used here for a secondary purpose. In this case, the OCT detector 32 may be both an imaging detector (one- or two-dimensionally resolving camera) or a non-imaging detector (for example a photodiode). In the case of a "balanced detection", the OCT detector 32 may also comprise multiple non-imaging detectors. Of which type the OCT detector 32 is depends on the OCT measuring method. Both variants are in principle compatible with all of the OCT measuring methods, in particular including with SD-OCT, SS-OCT and TD-OCT.

The alignment of the correct image angle takes place in one embodiment with the aid of the fixation light source 40, which optionally comprises a self-illuminating display. The patient is for example offered symmetrical, luminous patterns, which are set in such a way that the patient ultimately aligns the visual axis of the eye 22 to be measured with the axis of symmetry of the pupil of the apparatus 38a of the ophthalmological apparatus 10. Crosses, stars, squares, rings and rings with a dot in the center are especially suitable as patterns. In this way, suitable alignment of the viewing direction is achieved, because the patient intuitively positions itself in relation to the ophthalmological apparatus 10 in such a way that an image of the center of the fixation light pattern is formed on the center of the fovea of the retina 24. If the patient has failing visual acuity at the center of the fovea, the viewing direction can be specifically changed with the aid of the self-illuminating display, in that the fixation display that is offered is offset laterally on the display. This makes it possible to bring the center of the fovea into the center of the image of the ophthalmological apparatus 10 even when the eyesight of the patient is no longer sufficient at the center of the fovea.

By contrast, the patient would only notice incorrect lateral or axial positioning by possible vignetting effects, which however would be difficult for the patient to assess subjectively. For this reason, optical measurements by which incorrect lateral or axial positioning of the pupil of the eye 27 in relation to the pupil of the apparatus can be recorded objectively are provided. For this, in one embodiment the OCT detector 32 is used before the actual OCT measurement to measure the power of the OCT measuring radiation without using interference effects. Optionally, OCT illumination that has been reflected at the iris 28 is suitably suppressed, for example confocally. The power of the OCT measuring radiation that is measured by the OCT detector 32 is then proportional to the power of the OCT illumination that has passed the pupil of the eye 27. Consequently, the power of the OCT illumination is at a maximum when no OCT radiation is cut off at the iris 28. The power of the OCT illumination therefore represents a measure of the deviation of the pupil of the eye from the pupil of the apparatus. In this operating mode, the radiation of an OCT reference beam path (not represented) is optionally blocked, so that it does not reach the OCT detector 32. This requires a corresponding optical changeover device, for example an optical shutter. However, measurement may also be performed with reference radiation if the OCT detector 32 has sufficiently great intensity dynamics.

If, therefore, because of insufficient lateral or axial alignment of the pupil of the apparatus with respect to the pupil of the eye 27, OCT illumination 90 or backscattered OCT measuring radiation falls on the iris 28, the OCT radiation power at the OCT detector 32 is reduced correspondingly. This reduction is taken as a reason to request the patient in step S18 to make a modification in the alignment of the pupil of its eye, i.e. the pupil correction signal is generated. In order to establish what the maximum possible OCT radiation power at the time would be, this may be preceded by a corresponding reference measurement. In this case, the patient specifically carries out lateral and axial movements in all directions, while the OCT detector 32 measures the overall power. The maximum overall power that occurs during the reference measurement serves as a reference value. The power of the OCT measuring radiation represents an example of a measure of the deviation of the pupil of the eye from the pupil of the apparatus.

The request to the patient to readjust the pupil of the eye, that is to say the output of the pupil correction signal, may take place optically, acoustically or haptically, optically for example with the aid of the fixation light source 40. Spatially and/or temporally varying patterns make the patient aware that it has not yet aligned its eye sufficiently well with the ophthalmological apparatus 10. In particular for patients already with impaired eyesight, the request is preferably made acoustically and/or haptically. The request may be carried out iteratively, depending on whether the radiation power at the OCT detector 32 has increased or decreased since the last request. A haptic request may take place for example by means of a vibrating surface of the signal generating device 56. Only when the alignment of the pupil of the eye is sufficiently good does the vibration stop, or the vibration begin, or the vibration change. The vibrating surface may also be provided at the same time with sensitive properties, as in the case of a smart phone with a touchscreen, in order for example to actively initiate the start of the OCT measurement.

A variant of the step S16 improves the adjustment between the ophthalmological apparatus 10 and the pupil of the eye of the patient still further, in that a detector 48 is used in order to detect OCT radiation that is reflected at the cornea in a spatially resolved manner. The detector 48 preferably comprises a two-dimensionally resolving camera, but may alternatively also include an optical position sensor. It is important for this embodiment that the OCT radiation that is generated by the OCT radiation source 30 and is reflected at the cornea, or at least its centroid, is reflected back on itself when the OCT radiation falls centrally through the cornea, and consequently also through the pupil of the eye 27 of the eye 22. The second optical unit 52 is designed in such a way that in this case a bright spot of light that is as small as possible is produced in the center of the detector 48. Therefore, as soon as there is an incorrect lateral positioning, the spot of light on the detector 48 is displaced. This has the advantage over the first variant that the direction of the incorrect positioning can also be measured and indicated to the patient. An incorrect axial positioning can be detected on the basis of the size of the spot of light. For this, a 2D camera can be used as the detector 48; a PSD would be unsuitable, since it would only record the centroid of the spot of light.

Figure 5:
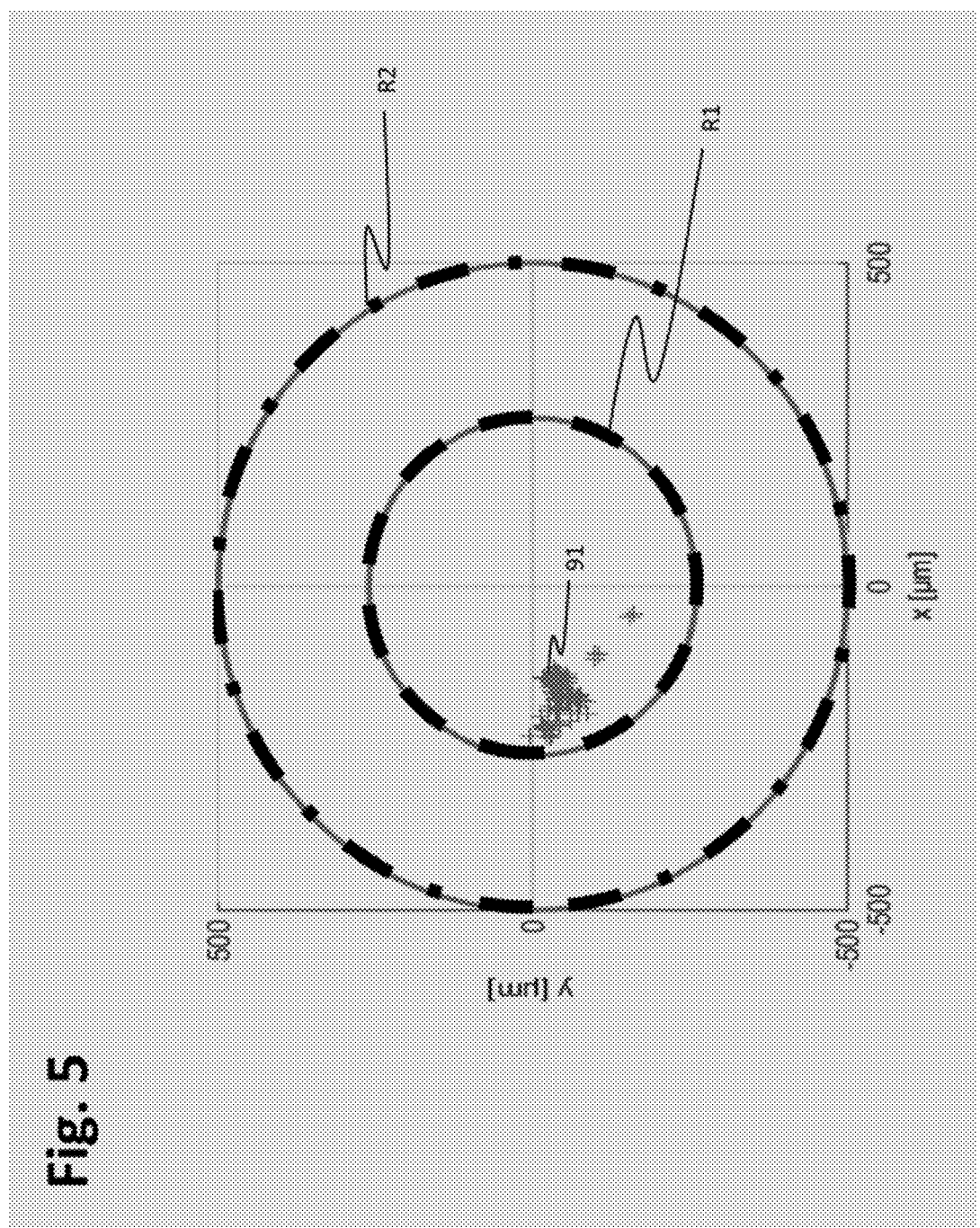
FIG. 5 shows a representation of prescribed limit values for a measure of a deviation between a position of the pupil of the eye and a position of the pupil of the apparatus.

FIG. 5 shows an actual measurement on a human eye 22 over a time period of five seconds, in which the position of the pupil was determined at intervals. The center 91 of the pupil of the eye 27/iris 28 (pupil positions) at a specific point in time is respectively represented by a cross. An outer radius of acceptance R2 represents the region in which the center 91 should in any event be located during the OCT measurement. The inner radius of acceptance R1 represents the region in which the center of the pupil/iris 28 is ideally located during the OCT measurement. As can be seen from the distribution of the crosses, over time the center 91 of the pupil of the eye 27 drifts laterally by typically a few hundred μm. Microsaccades can additionally lead to greater deflections for a short time (isolated crosses), the eye 22 then generally returning to the previous position. The outer radius of acceptance R2 and the inner radius of acceptance R1 represent examples of the prescribed limit value.

FIG. 6 shows the interaction of the iris detector 66 with the fixation light source 40 and the OCT measurement. The purpose of this specific interaction is that the patient can carry out a good-quality OCT measurement of its retina 24 on its own without the aid of a fully automatic alignment system and without the aid of a second person.

In a phase A (steps S14 to S20), the patient approaches the ophthalmological apparatus 10. The patient sees the fixation light pattern. At first, the patient possibly does not see the fixation light pattern sharply yet, because it is still in the orientation phase. It can perform the fixation setting now or later.

For the lateral alignment (i.e. perpendicularly in relation to the axis of symmetry of the pupil of the apparatus 38a), it is generally not sufficient that the patient orients itself just on the basis of a symmetrical vignetting of the fixation light. In particular, a uniform perception of brightness cannot be assumed in the case of patients with retinal damage, such as for example AMD. Such patients will therefore have particular difficulties in a lateral self-alignment with the aid of the vignetting of the fixation light. Therefore, in one embodiment the ophthalmological apparatus 10 has an iris detector 66. The iris detector 66 comprises a camera on which images of the pupil/iris 28 of the eye 22 or parts thereof or reflections from the front side of the cornea are formed. Optical units suitable for imaging likewise form part of the iris detector 66.

With the assistance of the positioning device 14, the iris detector 66 detects that the center of the pupil of the eye 27 (black circle with white cross as the center point in FIG. 6) is located outside the outer radius of acceptance (dash-dotted line). In phase A, the patient obtains the displayed fixation light pattern, which consists of a central fixation element (here: a star) and an arrow. The brightness and the distance of the arrow from the central fixation element can additionally provide the patient with directional and distance-related information in an intuitive way. The patient is preferably intended to perceive the central fixation element in such a way that an image thereof is formed at the center of the patient's fovea, whereby the viewing direction of the patient is established. The preferred perception can be ensured by the central fixation element being displayed more brightly than other elements on the fixation display.

In an optional configuration, the central fixation element flashes during phase A, i.e. as long as the patient has not yet sufficiently aligned itself. Optionally, the arrow may also flash at the same time. The flashing frequency is chosen such that it can be perceived well by the patient, but is not found to be disturbing. It preferably lies in the range of 1 . . . 20 Hz. The duty ratio (ratio of bright times to dark times) may be varied within wide limits, but also be in particular 1:1. During phase A, the OCT measurement in this example does not yet produce any usable OCT B scans (depth cross sections) of the retina 24.

In a phase B (steps S24 to S28), the patient has aligned itself so well that the center of the pupil of its eye 27 is within the radius of acceptance (dashed line). This desired state is brought to the attention of the patient by the central fixation element then being permanently lit up and the arrow disappearing. If the interferometric OCT length adjustment between the signal arm and the reference arm (OCT delay setting) already makes them match approximately, in phase B retina structures can already be seen with weak contrast, as indicated in the lower image of FIG. 6.

A phase C (steps S30 to S32) serves for optimally setting the OCT delay, that is to say the coherence condition, so that maximum contrast of the retina structures is produced in the OCT B scan. The optimum contrast setting is obtained by systematically changing the length of the reference beam path by means of an, optionally motorized, adjusting element and also a contrast analysis of the intensity distribution on the OCT detector 32. During phase C, the pupil/iris 28 of the patient ideally stays in the same position as that achieved in phase B. However, it must be expected that in phase C the pupil of the eye 27/iris 28 will drift out of the inner radius of acceptance because the setting operation can take up to a few seconds. In order not to have to abort the entire measurement and repeat it, the fixation light source 40 optionally provides the patient with feedback whenever it has left the inner radius of acceptance. As long as it is between the inner radius of acceptance and the outer radius of acceptance, this can be brought to the patient's attention intuitively by moderated feedback. The moderation may for example take the form that the amplitude of the flashing fixation light intensity is reduced, as represented in FIG. 6. In addition, the arrow may be displayed as less bright or as dashed lines. Otherwise, the functioning in phase C is the same as in phase A. Ideally, the patient returns to the inner radius of acceptance during phase C, if it has in the meantime left it.

During a phase D (step S34), the actual OCT measurement for the retinal imaging is carried out. In the case of a scanning OCT method, this is where the lateral scanning of the retina 24 takes place. In the case of a wide-field OCT method (full-field OCT), this is where a depth scan possibly takes place. Ideally, in phase D the center of the pupil of the eye 27/iris 28 is in the inner radius of acceptance and the OCT delay is optimally set. The best possible quality of the OCT B scan is then obtained. However, it is also possible to carry out the actual OCT measurement when the center of the pupil of the eye 27/iris 28 is between the inner radius of acceptance and the outer radius of acceptance. In this case, slight losses of quality of the OCT measurement must be expected. The advantage however is that the entire alignment process (A to D) does not have to be carried out again. This would only be necessary if the center of the pupil of the eye 27/iris 28 entered the region beyond the outer radius of acceptance.

Alternative fixation light patterns may also be used to give the patient directional information on the lateral alignment of its eye 22. For example, a ring may be depicted on the fixation light source 40 instead of an arrow. The position and size of the ring indicate to the patient how far away it is from the desired position, and in which direction. In the extreme case of when the patient is ideally aligned, the ring may shrink to a point at the location of the central fixation element.

A further configurational variant is to display two rings on the fixation light source 40, one of the rings taking the place of the central fixation element. Information is then transmitted to the patient by the two rings being all the more concentric the better the patient is aligned. Directional information can in turn be imparted to the patient by the position of the second ring in relation to the first ring. This variant with two rings is to be used with preference in the case of AMD patients if they have failing visual acuity in the central region of their sight (fovea).

In principle, other geometrical forms instead of points or rings, such as for example polygons, ellipses, stars or the like, can also be used as the fixation light pattern. The fixation light patterns may consist of luminous contours and/or of luminous areas. Furthermore, inverted fixation light patterns, in which the actual patterns appear dark against a bright background, can also be used. The fixation light patterns may be monochrome or multi-colored, and they may have colors that vary over time. The fixation light pattern may for example be designed in such a way that it changes from red to green when the alignment of the patient improves.

The fixation setting by the patient may be performed before phase A or within phases A to C. Since the patient performs the lateral alignment with its head or with its entire body, its hands are available for optimally setting the fixation setting in advance or at the same time, for example by turning a hand wheel.

The measures and apparatuses according to the invention that have been described in the exemplary embodiments for an OCT measuring device can also be used in an analogous way for other ophthalmological instruments, in particular for fundus cameras, keratometers and topographs of all types. Furthermore, the invention is also not restricted to OCT measuring apparatuses that form an image of the retina 24. It can similarly be used for OCT measuring apparatuses that form an image of the front portion of the eye 22 or biometrically measure the eye 22.

The invention claimed is:

1. A method for the self-examination of an eye of a patient by the patient itself by means of an ophthalmological apparatus, which has a front optical unit and a pupil of the apparatus, the method comprising
    a) the patient positioning the eye in relation to the ophthalmological apparatus;
    b1) determining a measure of a deviation between a first position of a pupil of the eye and a second position of a pupil of the apparatus;
    b2) depending on the measure of the deviation, generating a pupil correction signal, which indicates a direction and/or degree of the deviation, and outputting the pupil correction signal to the patient via an output device including a display, a loudspeaker or a vibration device, wherein, on the basis of the pupil position correction signal, the patient can perform a repositioning of the ophthalmological relative position between the eye and the apparatus with a smaller deviation;
    b3) repeating steps b1) and b2) until the measure of the deviation lies below a prescribed limit value;
    c1) checking whether a focal plane of the ophthalmological apparatus lies in a prescribed region in the eye;
    c2) if the focal plane does not lie in the prescribed region, generating and outputting to the patient either a focus signal with the aid of which the patient can bring the focal plane into the prescribed region or setting the focal plane by autofocus, c3) repeating step c1) and step c2) until the focal plane lies in the prescribed region; and
    d) examining the eye after completion of steps b1), b2), b3), c1) and c2.

2. The method as claimed in claim 1, further comprising forming an image of an iris of the eye on a spatially resolving iris detector by a first beam path, recording a position of the iris and using the position of the iris to determine a position of the pupil of the eye to determine the measure of the deviation.

3. The method as claimed in claim 2, wherein the iris is illuminated by an iris illumination source, radiation generated by the iris illumination source is coupled into the first beam path by a first beam splitter and/or the iris illumination source is arranged between the eye and the front optical unit.

4. The method as claimed in claim 1, further comprising forming an image of a cornea reflection of the eye is formed on a spatially resolving iris detector and determining a position of the cornea reflection on the iris detector, wherein the position of the cornea reflection on the iris detector represents a measure of the deviation.

5. The method as claimed in claim 1, wherein the ophthalmological apparatus comprises an OCT measuring device with an OCT beam source and an OCT detector, and step d) further comprises generating an OCT image.

6. The method as claimed in claim 5, wherein an OCT beam that is generated by the OCT radiation source is guided via an examination beam path to a retina of the eye, a radiation power of a reflection of the OCT beam at the retina is measured by the OCT detector, and the radiation power of the reflection of the OCT beam represents a measure of the deviation.

7. The method as claimed in claim 5, wherein an OCT beam that is generated by the OCT radiation source is guided via an examination beam path to a cornea of the eye, an image of a reflection of the OCT beam at the cornea is formed on a spatially resolved detector by a second beam path and a position of the reflection on the detector is determined, and the position of the reflection on the detector represents a measure of the deviation.

8. The method as claimed in one of claim 5, further comprising:
    e1) checking whether a coherence condition for a depth-resolved OCT imaging is satisfied;
    e2) if the coherence condition is not satisfied, either generating and outputting to the patient a coherence signal with the aid of which the patient can set the coherence condition, or automatically setting the coherence condition by the OCT measuring device; and
    e3) repeating step e1) and step e2) until the coherence condition is satisfied.

9. The method as claimed in claim 1, further comprising providing a fixation light source for generating a fixation light that is visible for the patient, and wherein the pupil correction signal comprises a temporal and/or spatial and/or spectral variation of the fixation light or a pattern offered by it.

10. The method as claimed in claim 9, wherein the fixation light of the pattern is varied depending on the measure of the deviation.

11. The method as claimed in claim 1, wherein the ophthalmological apparatus further comprises a manually and/or motor-variable headrest, individual presettings for prepositioning the ophthalmological apparatus in relation to the eye, and/or in relation to the focal plane being stored for different patients.

12. The method as claimed in claim 1, wherein a result of the examination that is generated in step d) is compared with a result of a comparative examination and, on the basis of comparison, a suggestion as to whether a further examination should be carried out by a physician is output to the patient.

13. An ophthalmological self-examination apparatus for an eye of a patient by the patient itself, comprising:
    an examination device for examining the eye, which has a front optical unit and a pupil of the apparatus;
    a positioning device, which records a measure of a deviation of a first position of a first pupil of an eye from second position of the pupil of the apparatus and, depending on the measure of the deviation, generates and outputs a pupil correction signal via an output device including a display, a loudspeaker or a vibration device, which indicates a direction and/or degree of the deviation, the positioning device outputting the pupil correction signal to the patient, who can on the basis of the pupil correction signal perform a repositioning of the relative position of the eye and the ophthalmological apparatus with a smaller deviation; and
    a focal plane adjusting device, which records whether a focal plane of the ophthalmological apparatus lies in a prescribed region, if the focal plane does not lie in the prescribed region of the eye the focal plane adjusting device generating a focus signal with the aid of which the patient can bring the focal plane into the prescribed region and outputting it to the patient or setting the focal plane by means of autofocus.

14. The apparatus as claimed in claim 13, characterized in that the ophthalmological self examination apparatus includes an optical coherence tomograph.

15. The apparatus as claimed in claim 13, characterized in that the ophthalmological self-examination apparatus includes a fundus imaging device.

16. The apparatus as claimed in claim 13, characterized in that a fixation light source for generating a fixation light that is visible for the patient is provided in the positioning device, the pupil correction signal comprising a temporal and/or spatial and/or spectral variation of the fixation light or a pattern offered by it.

17. The apparatus as claimed in claim 16, characterized in that the positioning device varies the fixation light or the pattern depending on the measure of the deviation.

\* \* \* \* \*

UNITED STATES PATENT AND TRADEMARK OFFICE
CERTIFICATE OF CORRECTION

PATENT NO. : 11,129,525 B2  
APPLICATION NO. : 16/348094  
DATED : September 28, 2021  
INVENTOR(S) : Peter Westphal et al.

Page 1 of 1

It is certified that error appears in the above-identified patent and that said Letters Patent is hereby corrected as shown below:

In the Claims

Column 26, Line 18, delete "The method as claimed in one of claim" and insert --The method as claimed in claim--

Column 27, Line 9, delete "Coherence Tomograph." and insert --Coherence Tomography.--

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*